(12) United States Patent
Hayton et al.

(10) Patent No.: US 8,123,082 B2
(45) Date of Patent: Feb. 28, 2012

(54) HAND-HELD DISPENSING DEVICE

(75) Inventors: Paul Graham Hayton, Bristol (GB); Tom Edward Walker, Bristol (GB); David Gary Cottle, Bristol (GB); Philip Walsh, Bristol (GB); Philip Beardsall, Örkelljunga (SE)

(73) Assignee: McNeil-AB (SE)

( * ) Notice: Subject to any disclaimer, the term of this patent is extended or adjusted under 35 U.S.C. 154(b) by 1026 days.

(21) Appl. No.: 12/009,669

(22) Filed: Jan. 22, 2008

(65) Prior Publication Data

US 2009/0183744 A1 Jul. 23, 2009

(51) Int. Cl.
*B67D 7/06* (2010.01)

(52) U.S. Cl. .................................. 222/183; 222/153.13

(58) Field of Classification Search .................. 222/183, 222/401, 402, 402.11, 402.12, 153.01, 153.11–153.13
See application file for complete search history.

(56) References Cited

U.S. PATENT DOCUMENTS

| | | | |
|---|---|---|---|
| 3,865,279 A | 2/1975 | James | |
| 3,918,451 A | 11/1975 | Steil | |
| 4,292,966 A | 10/1981 | Mono et al. | |
| 4,509,515 A | 4/1985 | Altounyan et al. | |
| 4,678,106 A | 7/1987 | Newell et al. | |
| 4,819,832 A | 4/1989 | Lawson | |
| 4,834,083 A * | 5/1989 | Byram et al. | 128/200.23 |
| 4,969,578 A | 11/1990 | Gander et al. | |
| 5,069,204 A * | 12/1991 | Smith et al. | 128/200.23 |
| 5,105,988 A | 4/1992 | Knickerbocker | |
| 5,217,004 A * | 6/1993 | Blasnik et al. | 128/200.23 |
| 5,255,823 A | 10/1993 | Tichy et al. | |
| 5,860,416 A | 1/1999 | Howlett | |
| 5,896,853 A | 4/1999 | Howlett | |
| 5,899,200 A | 5/1999 | McNary | |
| 6,062,214 A | 5/2000 | Howlett | |
| 6,164,275 A | 12/2000 | Van Iderstine | |
| 6,261,274 B1 | 7/2001 | Arghyris et al. | |
| 6,273,084 B1 | 8/2001 | Frid | |
| 6,299,900 B1 | 10/2001 | Reed et al. | |
| 6,405,727 B1 | 6/2002 | MacMichael et al. | |
| 6,745,760 B2 | 6/2004 | Grychowski et al. | |
| 6,792,941 B2 | 9/2004 | Andersson | |
| 6,971,552 B2 * | 12/2005 | Meshberg | 222/153.13 |
| 7,014,068 B1 * | 3/2006 | Cohen et al. | 222/321.9 |
| 7,047,967 B2 | 5/2006 | Knudsen | |

(Continued)

FOREIGN PATENT DOCUMENTS

CA 1327781 3/1994

(Continued)

*Primary Examiner* — Lien Ngo
(74) *Attorney, Agent, or Firm* — Karen G. Horowitz (57) ABSTRACT

A hand-held dispensing device having a dispenser incorporating: (i) a dispenser body defining a dispensing chamber for holding a substance; (ii) an outlet communicating with the dispensing chamber; (iii) a dispensing mechanism for dispensing the substance through the outlet; and (iv) an actuating member resiliently mounted for movement relative to the dispenser body to actuate the dispensing mechanism. The dispenser is operably connected to and manually slidable relative to a handle between a non-use position, and an operative position. The device further comprises a locking assembly for releasably locking the dispenser body to the handle in the operative position to prevent said manual sliding movement of the dispenser body, whereby a user may grasp the handle and effect manual movement of the actuating member relative to the handle and the dispenser body, against the action of the biasing member, to actuate the dispensing mechanism and dispense the contents of the dispensing chamber.

34 Claims, 9 Drawing Sheets

U.S. PATENT DOCUMENTS

| | | |
|---|---|---|
| 7,077,129 B2 | 7/2006 | Anderson et al. |
| 7,100,601 B2 | 9/2006 | Bruna |
| 7,104,424 B2 * | 9/2006 | Kolanus .................. 222/153.11 |
| 7,111,756 B2 | 9/2006 | Grey et al. |
| 7,651,009 B2 * | 1/2010 | Grant ........................... 222/183 |
| 2003/0136401 A1 | 7/2003 | Jansen et al. |
| 2003/0163089 A1 | 8/2003 | Bynum |
| 2004/0134488 A1 | 7/2004 | Davies |
| 2005/0028814 A1 | 2/2005 | Robertson et al. |
| 2005/0150488 A1 | 7/2005 | Dave |
| 2005/0154491 A1 | 7/2005 | Anderson et al. |
| 2005/0268909 A1 | 12/2005 | Bonney et al. |
| 2006/0071027 A1 | 4/2006 | Davies et al. |
| 2006/0081658 A1 | 4/2006 | Laidler et al. |
| 2006/0084908 A1 | 4/2006 | Bonney et al. |
| 2006/0151536 A1 | 7/2006 | Wong et al. |

FOREIGN PATENT DOCUMENTS

| | | |
|---|---|---|
| DE | 86282298 | 10/1988 |
| DE | 29818662 | 4/2000 |
| EP | 0506293 | 9/1992 |
| EP | 0613385 | 4/1997 |
| EP | 0744161 | 9/1999 |
| EP | 1029808 | 8/2000 |
| EP | 0864335 | 5/2005 |
| GB | 2348676 | 10/2000 |
| WO | 9325251 | 12/1993 |
| WO | 9509669 | 4/1995 |
| WO | 0185237 | 11/2001 |
| WO | 0230503 | 4/2002 |
| WO | 0243611 | 6/2002 |
| WO | 03080161 | 2/2003 |
| WO | 03086644 | 10/2003 |
| WO | 2004056413 | 7/2004 |

* cited by examiner

HAND-HELD DISPENSING DEVICE

FIELD OF THE INVENTION

The present invention relates to a hand-held dispensing device for dispensing a substance, in particular a substance in liquid form such as, for example, a nicotine formulation for use in treating smoking dependence.

SUMMARY OF THE INVENTION

It is known to provide hand-held dispensing devices for various substances, often where it is desired that the device be portable, for example in a handbag or pocket. Examples of such substances include perfumes and creams, as well as medical substances such as inhaler spray formulations and nicotine formulations for use in treating smoking dependence.

Often, the dispensing device will incorporate a dispensing mechanism in the form of a conventional aerosol dispensing mechanism or a spray pump mechanism, which is actuated to dispense the contents of a dispensing chamber holding the relevant substance.

There are a number of determining factors that might typically govern the design of such dispensers. For example, it may be desirable that the dispenser is manually operable using only a single hand; there may be a preference that the dispenser can be put into a "non-use" configuration, whereby accidental dispensing of the substance is prevented; it may be desirable to ensure that the dispensing chamber is prevented from mechanical shock which might otherwise damage the dispensing chamber, with consequent leakage of the substance; there may be a requirement, particularly in the case of certain medical substances, that the dispensing device be provided with "child resistant" features which tend to prevent operation of the dispensing mechanism by a child or accidental operation in general, for example when carrying the device in a pocket or handbag.

A number of the factors that determine the design of such dispensing devices are actually "competing" factors. For example, whilst it may be desirable that the device be provided with "child resistant" features, it is nevertheless desirable that the operation of the device is at the same time simple for adults to operate, including elderly people. This may be particularly important in the case of dispensing devices for medical substances, where it is desirable to reduce, or at least simplify, any accompanying instructions for using the device in order to minimise confusion and consequent incorrect operation of the device.

The design of hand-held dispensing devices can thus be a difficult balance between competing design factors, particularly when, often, the overriding aim is that the specific design of the device is one which is compact, portable and lends itself to mass-production.

It is an object of the present invention to seek to provide an improved hand-held dispensing device.

According to the present invention there is provided a hand-held dispensing device for dispensing a substance, the device comprising a dispenser incorporating:

i) a dispenser body defining a dispensing chamber for holding the substance;
ii) an outlet in communication with the dispensing chamber;
iii) a dispensing mechanism for dispensing the contents of the dispensing chamber through the outlet and
iv) an actuating member mounted for movement relative to the dispenser body to actuate the dispensing mechanism;

the dispenser being operably connected to a handle for manual sliding movement relative to the handle from a non-use position, in which the handle covers the outlet, to an operative position, in which the outlet is uncovered;

the device further comprising a locking assembly for releasably locking the dispenser body to the handle in the operative position to prevent said manual sliding movement of the dispenser body, whereby a user may grasp the handle and effect manual movement of the actuating member relative to the handle and the dispenser body so as to actuate the dispensing mechanism and dispense the contents of the dispensing chamber through the uncovered outlet.

Preferably, the actuating member is resiliently mounted for movement relative to the dispenser body against the action of a biasing member wherein, with the dispenser in the operative position, a user may effect said manual movement of the actuating member relative to the handle and the dispenser body, against the action of the biasing member.

Preferably, the dispenser is operably connected to the handle for relative, manual, sliding movement along a line of action of said biasing member, the biasing member maintaining the dispenser body and actuating member in substantially fixed, spatial relation to one another during said sliding movement from the non-use position to the operative position.

The locking assembly may be further configured for releasably locking the dispenser body in the non-use position to prevent said manual sliding movement of the dispenser to the operative position.

In one embodiment, the actuating member is provided with a stop that engages an abutment on the handle when the dispenser is in said non-use position for preventing actuating movement of the actuating member, relative to the dispenser body.

The actuating member is preferably in the form of a dispenser head incorporating the outlet, the dispenser head being mounted at one end of the dispenser body for manual depression relative to the dispenser body, against the action of said biasing member, to actuate the dispensing mechanism. The dispenser head may be configured to block the opening in the housing when the dispenser is retracted to said non-use position.

The handle may be a hollow housing which slidably receives the dispenser for manual sliding movement substantially along the axis of said depression of the dispenser head, the dispenser being manually slidable between said operative position, in which the dispenser head projects outwardly through an opening in the housing, and said non-use position, in which the dispenser is retracted within the housing.

The dispenser head may be dimensioned to engage the housing in a telescopic fit, the length of the dispenser head being such that the dispenser head blocks the opening in the housing over the full range of manual sliding movement of the dispenser between said non-use position and said operative position.

In one embodiment, the section of the wall of the housing is cut-away adjacent the opening such that a user may manually engage the dispenser head directly in said retracted, non-use position and effect manual sliding movement of the dispenser head, relative to the housing, to move the dispenser from the non-use position to the operative position, said biasing member maintaining the dispenser body and dispenser head in substantially fixed relation during said sliding movement.

The dispenser head may comprise a peripheral skirt defining a hollow interior head region communicating with the interior of the housing, the locking assembly comprising a locking lever mounted to the dispenser body at a fulcrum located inside the hollow interior head region, the locking lever having a latching element which is displaceable, by pivotal movement of the locking lever, into and out of latching engagement with the housing.

Conveniently, the locking lever is urged by a resilient element in the direction to displace the latching element into latching engagement with the housing.

In a further embodiment, the peripheral skirt is provided with a window which is aligned with the cut-away section of the housing, whereby a user may apply manual pressure to the locking lever, through said cut-away section and the window in the peripheral skirt, to effect said pivotal movement of the locking lever against the action of the resilient element in the direction to displace the latching element away from latching engagement with the housing.

Optionally, a transmission plate is displaceably mounted on the peripheral skirt at the aperture, for transmitting to the locking lever said manual pressure applied to the transmission plate. The transmission plate may be hingedly mounted on the exterior of the peripheral skirt and dimensioned for inward tilting movement through the window to engage the locking lever. Additionally, the transmission plate may be slidably mounted on the peripheral skirt for sliding movement relative to the window between an aligned position, allowing said inward tilting movement of the transmission plate through the window, and a mis-aligned position, in which the edge of the aperture prevents inward tilting movement of the transmission plate through the aperture. The transmission plate may conveniently be resiliently biased towards said mis-aligned position and is slidable against the action of said bias into the aligned position.

The exterior of the housing may incorporate a flat face-section.

The dispensing mechanism may be a pump mechanism, whilst the outlet may be a spray nozzle.

The dispensing chamber may contain a substance in liquid form, for example a nicotine formulation or other formulation.

Where the substance comprises a nicotine formulation, the dispenser body is preferably made from a material selected from one or more of or a mixture of glass, a copolymer of acrylonitrile and methyl acrylate (Barex®), a cyclic olefin copolymer (COC), polymers based on dimethyl-2,6 naphthalene dicarboxylate or 2,6-naphthalene dicarboxylic acid monomers, such as polyethylene naphthalate (PEN) and polytrimethylene naphthalate (PTN), liquid crystal polymers (LCP), preferably LCPs comprising hydroxy benzoic acid and hydroxy naphthalenic acid, said materials being optionally mixed with one or more of polymers, selected from polyacrylonitrile (PAN), polyamide (PA), polyvinylidene chloride (PVDC), fluoropolymers, ethylene vinyl alcohol copolymer (EVOH), polyvinyl alcohol (PVA), ionomers, polyethylene (PE), polypropylene (PP) and polyethylene terephtalate (PET).

BRIEF DESCRIPTION OF THE DRAWINGS

In order that the invention may more readily be understood, embodiments of the invention will now be described in more detail, by way of example, with reference to the accompanying drawings in which:

FIG. 1b is a perspective view showing part of the dispensing device of FIG. 1a;

FIG. 1c is a perspective view showing part of the dispensing device of FIG. 1a;

FIGS. 3a to 7e are perspective views, partly in cut-away section, illustrating step-by-step movement of the dispensing device from the non-use configuration to a dispensing configuration.

DETAILED DESCRIPTION OF THE DRAWINGS

For the avoidance of any doubt it is noted that the Figures are exemplary and are not intended to limit the invention, but rather serve to illustrate one possible embodiment of the invention as set out in the appended claims.

Figure 1A:
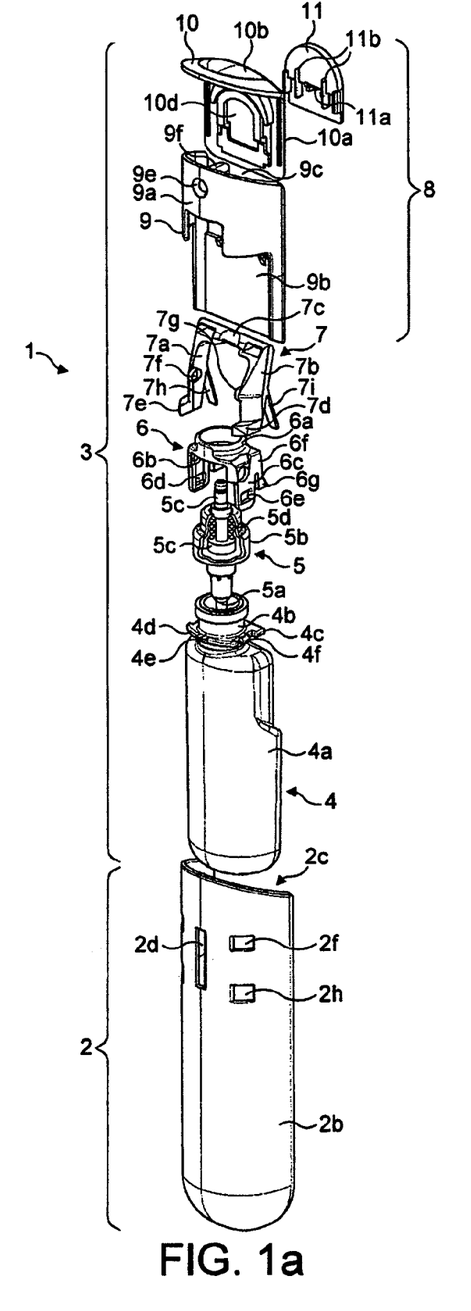
FIG. 1a is an exploded schematic view illustrating the principal components of a dispensing device.

FIG. 1a is an exploded view of a dispensing device 1, showing the principal sub-components of the dispensing device 1.

In overview, the dispensing device 1 comprises a housing 2 and a dispenser 3 slidably received within the housing 2.

The housing 2 is an elongate, hollow, body, open at one end and having a generally D-shaped cross-section defined by a flat rear wall 2a (see FIG. 2b) and a curved front wall 2b. A section of the flat rear wall 2a is recessed or "cut away" adjacent the open end of the housing 2 such that the curved front wall 2b and flat rear wall 2a together form an irregular opening 2c (the shape of which is best appreciated by referring to FIG. 2b). It should be appreciated here that the term "cut away" does not imply that the relevant section has necessarily been formed by cutting out a pre-existing section of the front wall. Indeed, the entire housing 2 may be formed in one piece (including the cut-away section) by, for example, appropriate moulding of a suitable rigid plastics material.

Figure 2A:
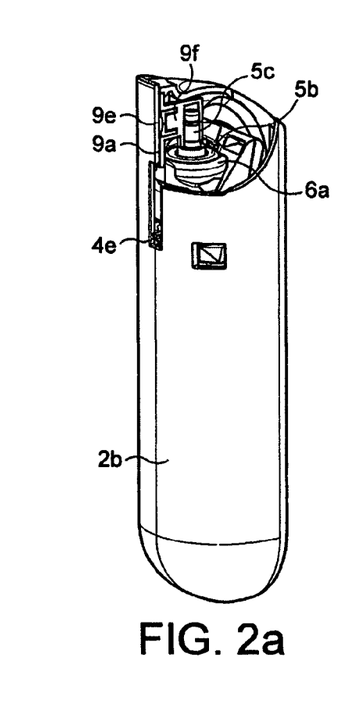
FIGS. 2a to 2e are perspective views, partly in cut-away section, showing the assembled dispensing device in a non-use configuration.

An elongate, generally vertical, central slot 2d is provided in the curved front wall 2b, opposite the "cut away" section of the rear wall 2a. A pair of smaller, square apertures 2e, 2f is positioned at the upper end of the central slot 2d, the apertures 2e, 2f being positioned either side of the central slot 2d, diametrically opposite one another. A second pair of corresponding square apertures 2g, 2h is positioned at the lower end of the central slot 2d in like manner, such that the four apertures 2e, 2f, 2g, 2h are positioned at the four corners of a notional square (see FIG. 2c). The rear wall 2a is provided with a pair of guide slots 2i, 2j running parallel to one another and the central slot 2d, below the cut-away section of the rear wall 2a (see FIG. 2b).

The dispenser 3 comprises five principal sub-components: a dispenser body in the form of a phial 4, a dispensing mechanism in the form of a pump mechanism 5, a collar 6 for securing the pump mechanism 5 to the phial 4, a locking lever 7 and an actuating member in the form of a dispenser head 8 (the dispenser head 8 itself being shown in exploded view in FIG. 1a).

The phial 4 is of a generally conventional shape comprising a main body portion 4a having a D-shaped cross-section and defining a dispensing chamber for holding a substance, and a hollow, cylindrical neck portion 4b that defines an open 'mouth'.

The phial 4 may be formed from any suitable material using any suitable method, for example by blow-moulding a plastics material or the like. In the case where the dispensing device is intended to hold a nicotine formulation, the corresponding dispensing body, for example the phial 4, is preferably formed from a "nicotine-inert" material that essentially does not absorb or react with the nicotine formulation and that also constitutes a satisfactory barrier against migration of oxygen and water, for example glass, a copolymer of acrylonitrile and methyl acrylate (Barex®) or a cyclic olefin copolymer (COC), and combinations thereof. Other suitable materials of which the phial 4 may be formed include materials selected from polymers based on dimethyl-2,6 naphthalene dicarboxylate or 2,6-naphthalene dicarboxylic acid monomers, such as polyethylene naphthalate (PEN) and polytrimethylene naphthalate (PTN), liquid crystal polymers (LCP), preferably LCPs comprising hydroxy benzoic acid and hydroxy naphthalenic acid, and combinations thereof. Suitable materials also include the captioned materials mixed with one or more of other polymer(s), selected from the group consisting of polyacrylonitrile (PAN), polyamide (PA), polyvinylidene chloride (PVDC), fluoropolymers, ethylene vinyl alcohol copolymer (EVOH), polyvinyl alcohol (PVA), ionomers, polyethylene (PE), polypropylene (PP) and polyethylene terephtalate (PET).

The neck portion 4b incorporates a peripheral flange 4c of broadly rectangular shape but including a curved front edge 4d corresponding to the curved inner face of the front wall 2b of the housing 2. The front edge 4d is provided with a guide projection 4e and a pair of mounting projections 4f (of which only one mounting projection is visible in FIG. 1a) respectively located on the opposite, shorter sides of the generally rectangular peripheral flange 4c.

The pump mechanism 5 is of generally conventional construction and is shown only very schematically in partial cross-section in FIG. 1a. The pump mechanism 5 comprises an intake tube 5a (only the very top of which is visible in FIG. 1a) for drawing liquid from within the main body 4a of the phial 4, a cylindrical pump housing 5b defining an internal pump chamber (not shown), communicating with the intake tube 5a, and a piston member 5c mounted for movement within the pump chamber, against a biasing member in the form of coil spring 5d (shown in cross-section in FIG. 1a), for displacing the contents of the pump chamber up through a bore (not shown) in the piston member 5c and out through the hollow stem portion of the piston member 5c in conventional manner.

The pump housing 5b is seated on the rim of the mouth of the phial 4, thus sealing the mouth of the phial 4, with the intake tube 5a extending down into the dispensing chamber defined by the body 4a of the phial 4.

The collar 6 functions to clamp the pump mechanism 5 in the aforementioned sealing engagement with the mouth of the phial 4 and comprises a ring portion 6a and a pair of diametrically opposed arms 6b, 6c depending from the ring portion 6a. Each arm 6b, 6c has a degree of resilience and is also provided with a respective aperture 6d, 6e at its lower end. The collar 6 is further provided with a pair of resilient secondary, legs 6f which terminate in respective ramp elements 6g (only one of which is visible in FIG. 1a) for locking the dispenser head 8 to the collar 6 in a manner described in more detail below.

To clamp the pump mechanism 5 to the phial 4, the pump housing 5b is first seated on the rim of the mouth of the phial 4 (with the intake tube 5a extending down into the phial 4) and then the collar 6 is pressed down over the top of the pump housing 5b with the arms 6b, 6c extending down either side of the pump housing 5b, whereby the arms 6b, 6c are resiliently deformed by the sides of the pump housing 5b before respectively engaging with the mounting projections 4f in a "snap-fit". The pump housing is thus securely clamped between the rim of the mouth of the phial 4 and the ring portion 6a of the collar 6, with the hollow stem of the piston member 5c extending vertically upwardly above the ring portion 6a of the collar 6 (see, for example, FIG. 2a).

Still referring to FIG. 1a, the locking lever 7 comprises a pair of legs 7a, 7b depending from the ends of a connecting yoke portion 7c that extends perpendicularly to each of the legs 7a, 7b.

Each leg 7a, 7b incorporates a latching element in the form of a respective projecting "foot" 7d, 7e positioned at the distal end of the respective leg 7a, 7b, an inwardly projecting lug 7f, 7g, positioned at the "knee" of the respective leg 7a, 7b, and an elongate, resilient elements 7h, 7i extending rearwardly from the back of the "knee" of the respective leg 7a, 7b and terminating opposite the "heel" of the respective projecting "foot" 7d, 7e.

The legs 7a, 7b are provided with sufficient resilience to allow "snap-fitting", rotating engagement of the lugs 7f, 7g with respective circular apertures 6d, 6e on the arms 6b, 6c of the collar 6, the locking lever 7 thus being secured to the collar 6 such that it may rotate with respect to the collar 6, about an axis passing through the lugs 7f, 7g.

The dispenser head 8 comprises a face portion 9, a cap portion 10 and a transmission plate 11.

The face portion 9 has a generally D-shaped cross-section, for telescopic, sliding engagement within the housing 2, and is defined by a curved front wall 9a and a flat rear wall 9b. In similar manner to the rear wall 2a of the housing 2, the upper section of the flat rear wall 9b is "cut away" to form an irregular shaped opening 9c in the face portion 9 corresponding to the irregular shaped opening 2c in the housing 2. In addition, the lower section of the curved front wall 9a is similarly "cut away". As best shown in FIGS. 2d and 2e, a pair of slide projections 9d is provided along the bottom edge of the outer face of the rear wall 9b for slidably engaging with the guide slots 2i, 2j on the rear wall 2a of the housing 2. In addition, a pair of ramp projections 9g is provided along the top edge of the inner face of the rear wall 9b (i.e. immediately below the cut away section in the rear wall 9b) for locking engagement with the ramp elements 6g provided on the collar 6.

An outlet 9e is provided in the front wall 9b. The outlet 9e, which may be any conventional spray outlet, is in fluid communication with a supply passage 9f formed as an integral part of the face portion 9 and extending back into the opening 9c.

The cap portion 10 comprises a flat rear wall 10a, dimensioned to fit the cut-away section of the corresponding rear wall 9b of the face portion 9, and a cantilevered top portion 10b projecting from the upper edge of the rear wall 10a and having a D-shaped cross-section corresponding to the cross section of the face portion 9.

The cap portion 10 is fixedly fitted within the opening 9c of the face portion 9 such that the rear wall 10a and rear wall 9b together form a peripheral skirt and the rear wall 10a defines a stop in the form of a ridge 10c, the function of which will become clearer below.

Figure 1B:
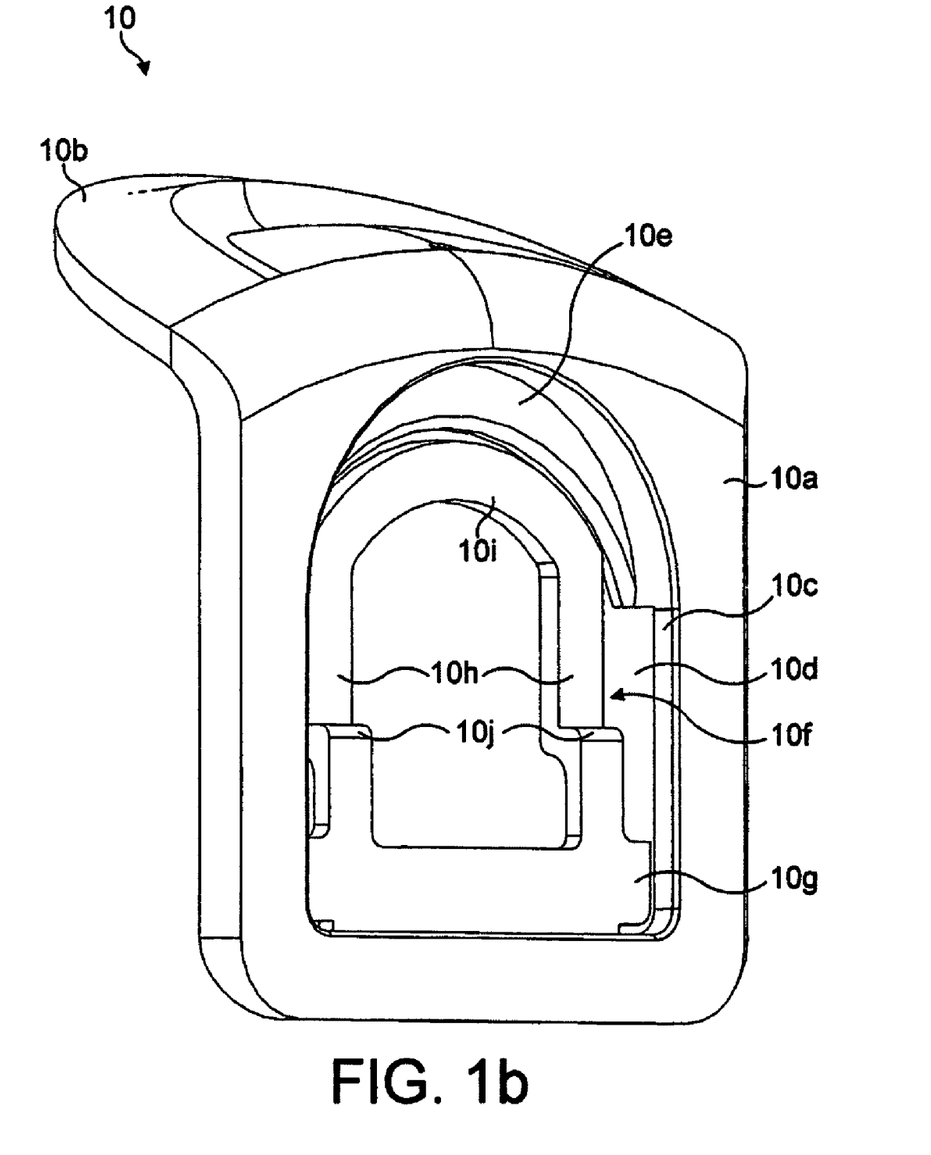
Figure 1C:
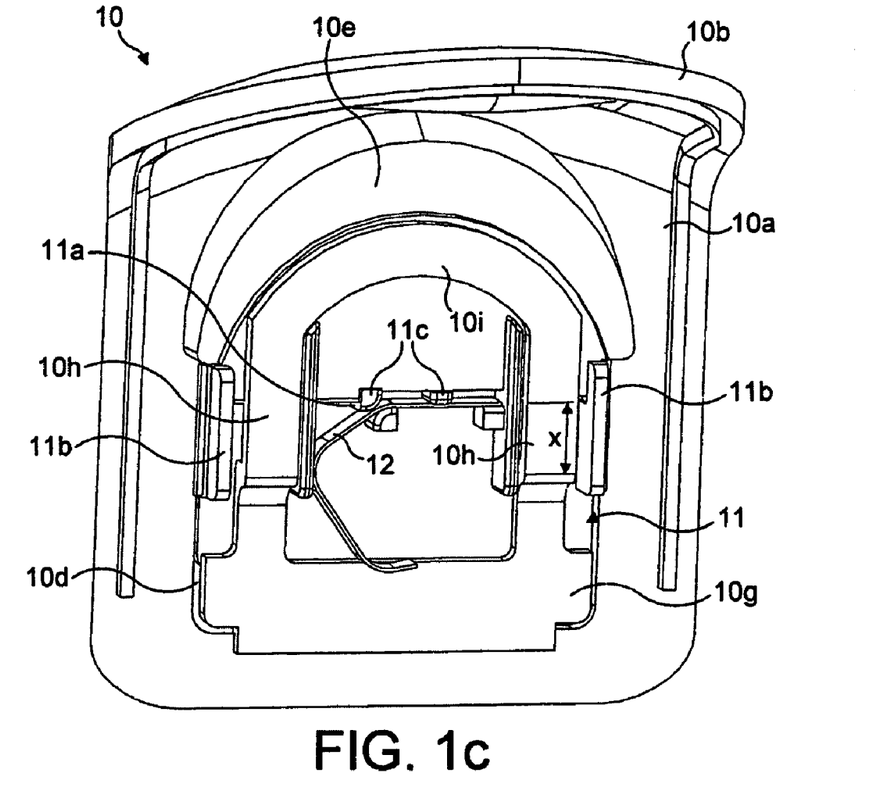

The rear wall 10a (and hence the aforementioned peripheral skirt) is provided with an arched window 10d, shown more clearly in FIGS. 1b and 1c. The upper, arched edge of the window 10d is defined by a crescent-shaped shoulder 10e, recessed from the rear wall 10a, and the straight, lower edge of the window 10d is provided with a hinged, arched frame 10f on the inside of the rear wall 10a, attached along the lower edge of the aperture 10d by means of a "living" hinge.

The arched frame 10f comprises: a straight frame section 10g running along the lower edge of the arched window 10c, a pair of parallel frame sections 10h running parallel with the straight sides of the arched window 10d, but spaced inwardly from the sides of the arched window 10d, and an arched frame section 10i running along the inner edge of the shoulder 10e at the top of the arched window 10d. The frame members 10h are each provided with a step 10j approximately one third of the way up the frame sections 10h (measured from the lower frame section 10g). The steps 10j accommodate the off-set between, on the one hand, the lower edge of the arched window 10d and, on the other hand, the curved shoulder 10e defining the upper edge of the window, an upper region of the frame members 10h thus being recessed from a lower region of the frame members 10h (see FIG. 1b in particular).

A C-shaped sprung metal member 12 is fixedly attached to the lower frame section 10g, the function of which will become apparent below.

Referring now to the transmission plate 11, this has a similar outline shape to the arched window 10d. A step 11a is formed on the inner face of the transmission plate 11, the step 11a having a depth corresponding to the depth of the steps 10j on the frame sections 10h, but being positioned halfway up the inner face of the transmission plate 11. The inner face of the transmission plate 11 is also provided with guide channels 11b, for slidably engaging the parallel frame sections 10h of the frame 10f, and with an arrangement of locating members 11c positioned adjacent the step 11a for locating the upper arm of the C-shaped sprung metal member against the underside of the step 11a.

The transmission plate 11 is slidably mounted to the hinged frame 10e by engaging the guide channels 11b with the parallel frame sections 10h, and the upper arm of the sprung metal member 12 is located against the underside of the step 10a using the locating members 11c. The transmission plate 11c an then be securely maintained in sliding engagement with the frame 10f by, for example, gluing the upper arm of the sprung metal member 12 in place against the underside of the step 11a. Alternatively, the locating members can be configured to securely clip the transmission plate 11 to the sprung metal member 12, without the need for gluing.

Figure 2B:
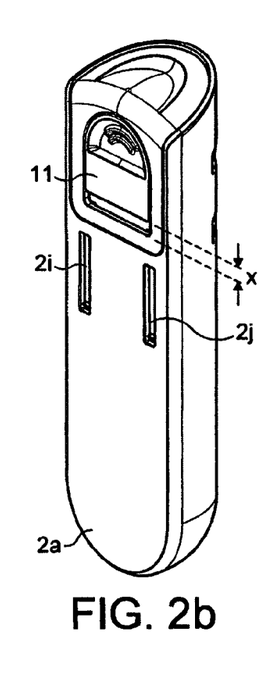
Figure 2C:
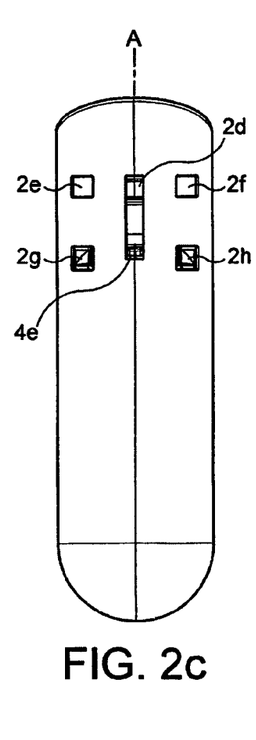
Figure 2D:
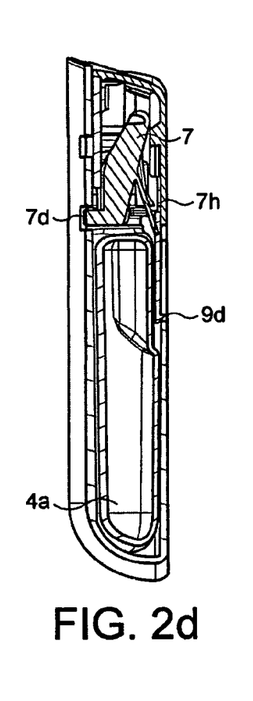
Figure 2E:
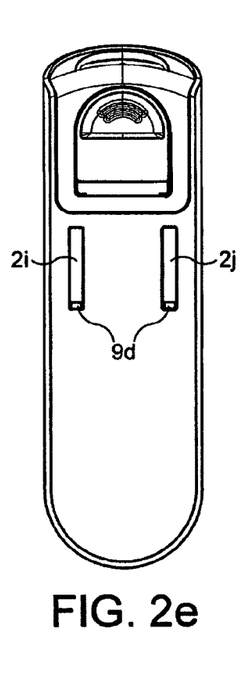
Figure 3A:
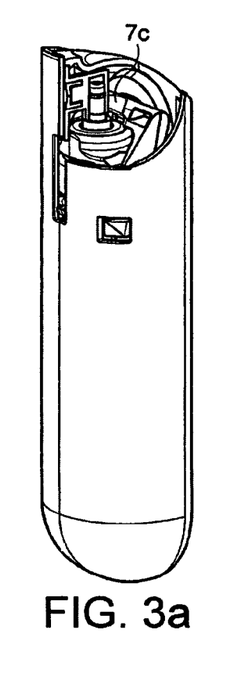
Figure 3B:
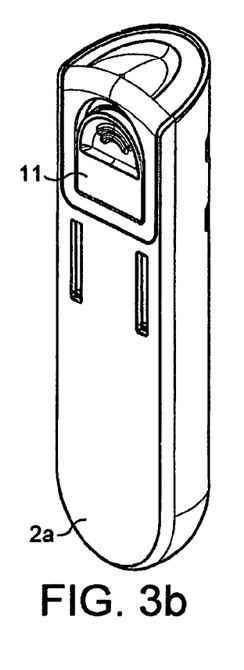
Figure 3C:
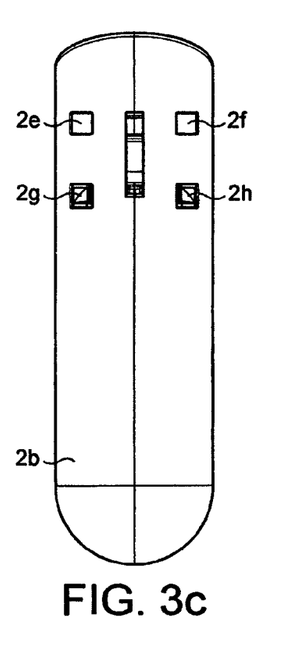
Figure 3D:
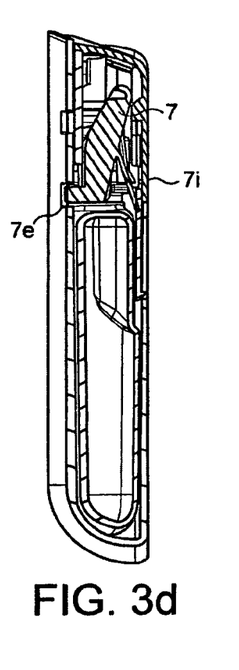
Figure 3E:
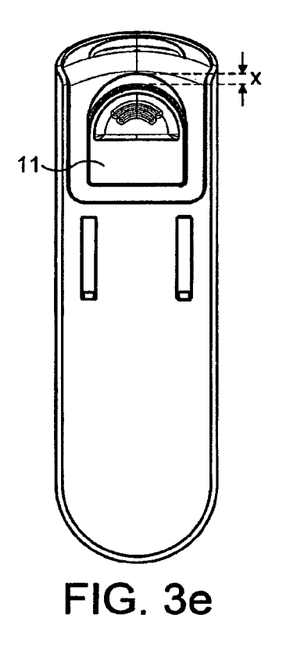
Figure 4A:
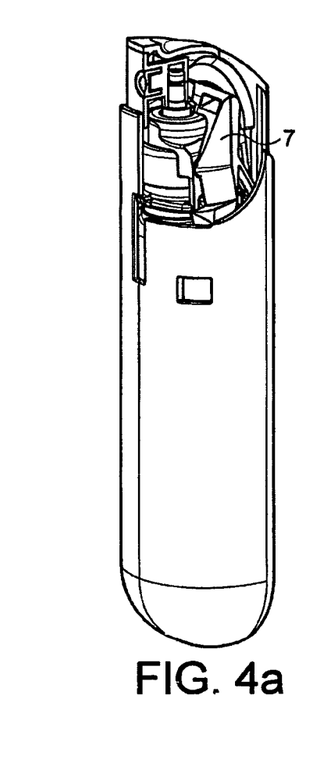
Figure 4B:
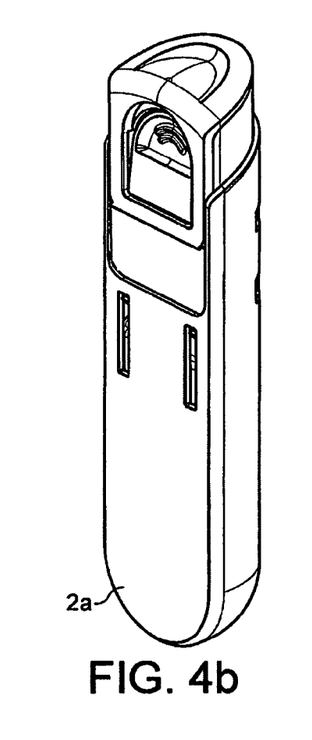
Figure 4C:
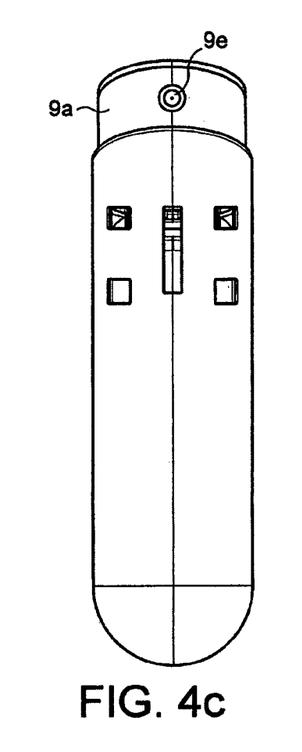
Figure 4D:
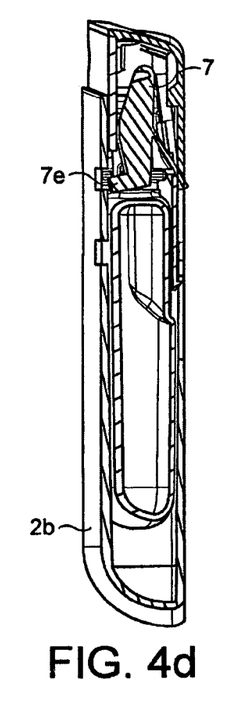
Figure 4E:
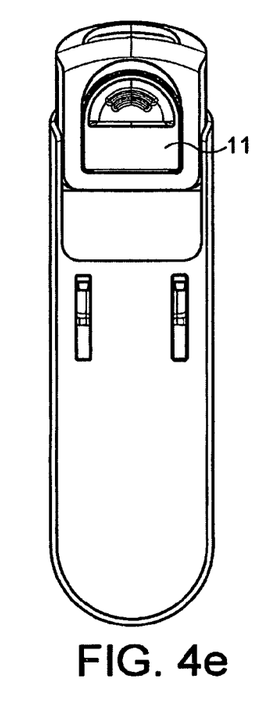

In any event, with the transmission plate 11 fixedly attached to the upper arm of the sprung metal member 12, the sprung metal member 12 acts to resiliently bias the transmission plate 11 into the position shown in FIGS. 1c and 2b, whereby the transmission plate 11 bears against an edge of the rear wall 10a formed by the recessed shoulder 10e. With the transmission plate in this misaligned position, inward tilting movement of the transmission plate 11 is prevented by the shoulder 10e.

It will be appreciated, referring to 2b in particular, that in the aforementioned misaligned position, the lower edge of the transmission plate 11 is spaced a distance x from the lower edge of the arched window 10d. Similarly, referring to FIG. 1c, the step 11a on the inner face of the transmission plate 11 is spaced a distance x above the steps 10j. The transmission plate 11 can thus be slid down a distance x, against the bias of the resilient sprung metal member, so that the transmission plate 11 abuts against the steps 10j and the lower edge of the arched window 10d. In this aligned position, the curved upper edge of the transmission plate 11 clears the shoulder 10e, thus allowing inward tilting movement of the transmission plate 11 (supported on the hinged frame 10f) through the arched window 10d.

The dispenser head 8 is mounted for movement relative to the phial 4 to actuate the pump mechanism 5.

Specifically, the dispenser head is resiliently mounted on the pump mechanism 5 for actuating movement relative to the phial 4, against the action of the coil spring 5d, to actuate the pump mechanism 5 and dispense the contents of the phial 4 through the outlet 9e.

To mount the dispenser head 8, the dispenser head 8 is pressed down onto the pump mechanism 5 such that the down pipe of the supply passage 9f engages the hollow stem of the piston member 5c to form a closed passageway between the phial 4 and the outlet 9e, via the internal pump chamber in the pump mechanism 5. As the dispenser head 8 is pressed down onto the pump mechanism 5, engagement of the ramp projections 9g and ramp elements 6g serves to "snap-fit" the rear wall 9b down over the collar 6 whereby the ramp projections 9g and ramp elements 6g subsequently limit upward movement of the dispenser head 8 relative to the collar 6 (and hence the phial 4).

To assemble the dispensing device 1, the various sub-components of the dispenser 3 may be assembled in the manner described above and then the dispenser 3 may be slidably engaged with the housing 2 by sliding the housing over the phial 4 and "snap-fitting" the guide projection 4e and slide projections 9d within the central slot 2d and guide slots 2i, 2j respectively (see FIGS. 2d and 2e in particular).

It will be appreciated that in the assembled dispensing device 1, the central slot 2d and guide slots 2i, 2j accommodate a limited range of sliding movement of the dispenser 3 relative to the housing 2 along the axis A, whilst nevertheless keying the dispenser 3 to the housing 2 to prevent relative rotation of the dispenser 3 and the housing 2.

The operation of the dispensing device 1 will now be described with reference to FIGS. 2 to 8, which show the assembled dispensing device 1 in various configurations.

Thus, FIGS. 2a to 2e show corresponding views of the assembled dispensing device 1 in initial non-use position, wherein the dispenser 3 is retracted within the housing 2.

Figure 5A:
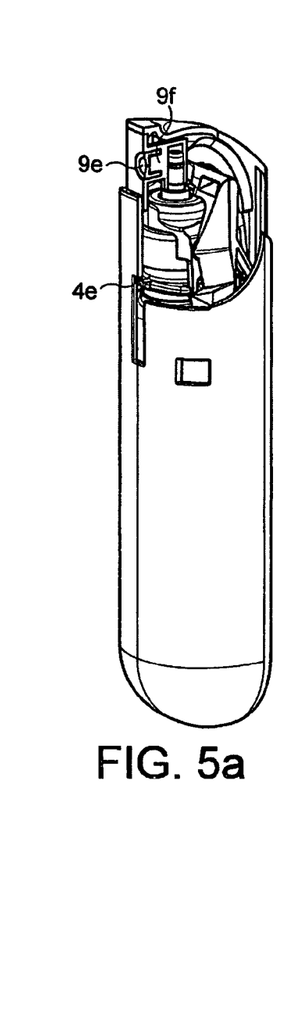
Figure 5B:
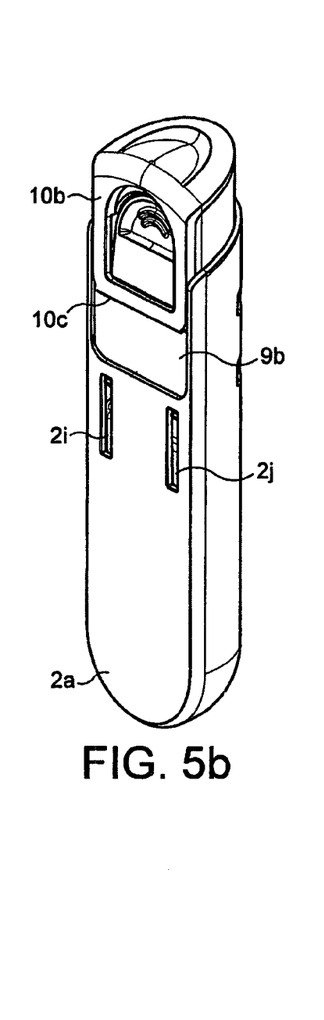
Figure 5C:
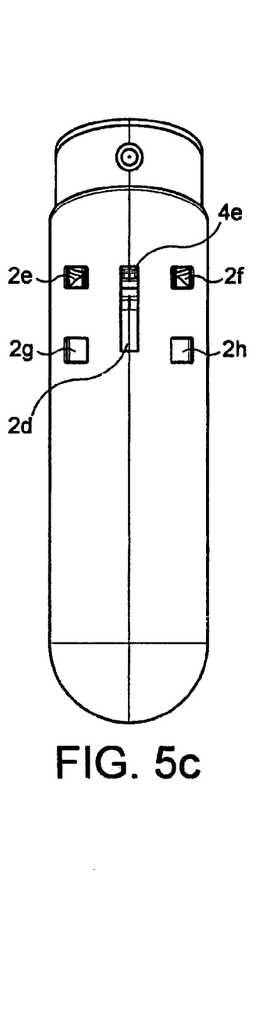
Figures 5D, 5E:
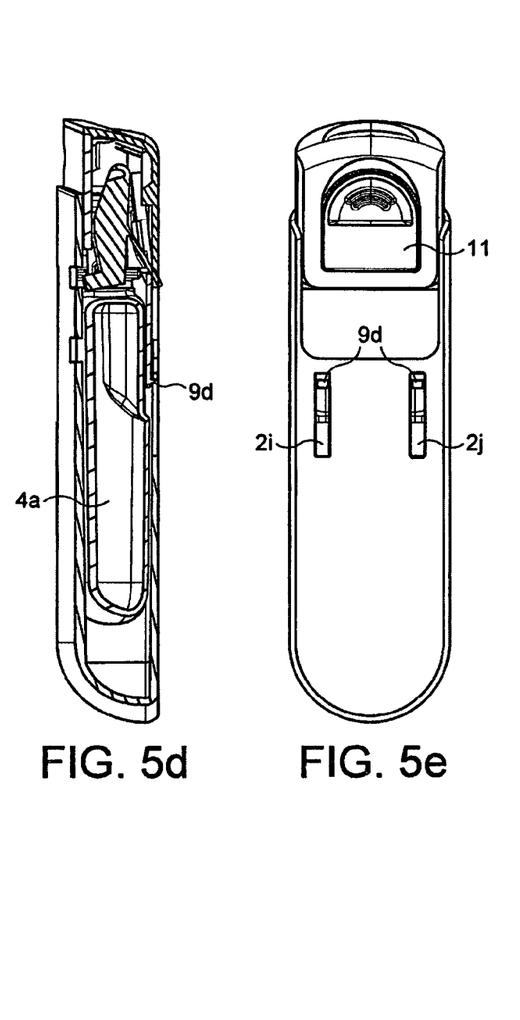
Figures 6A, 6B:
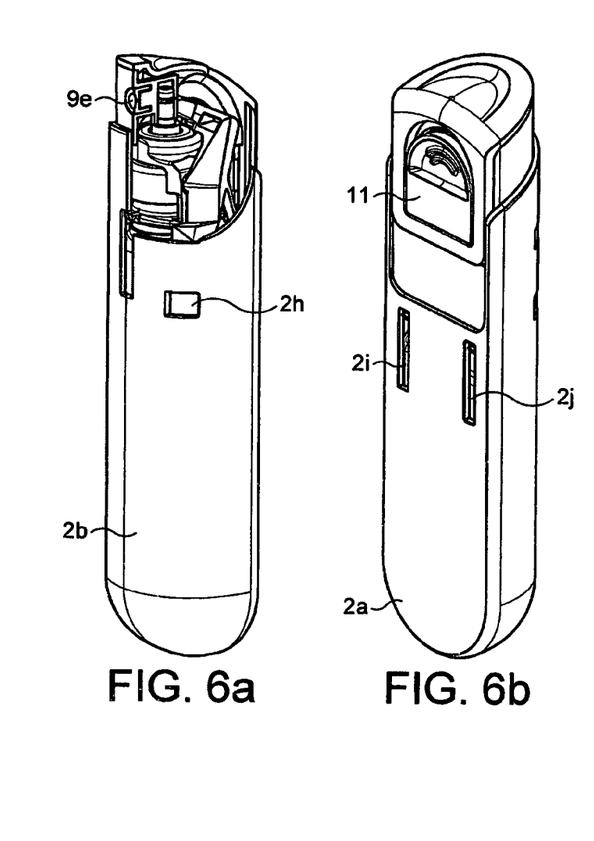
Figure 6C:
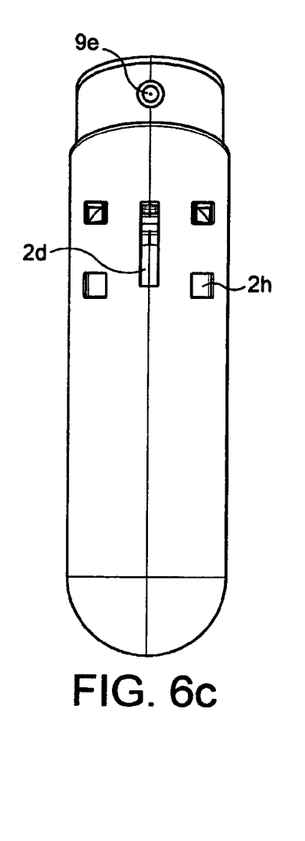
Figure 6D:
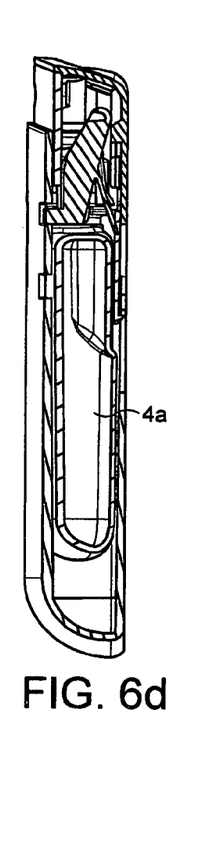
Figure 6E:
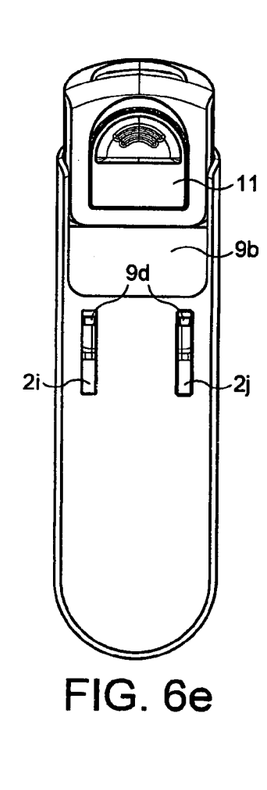
Figure 7A:
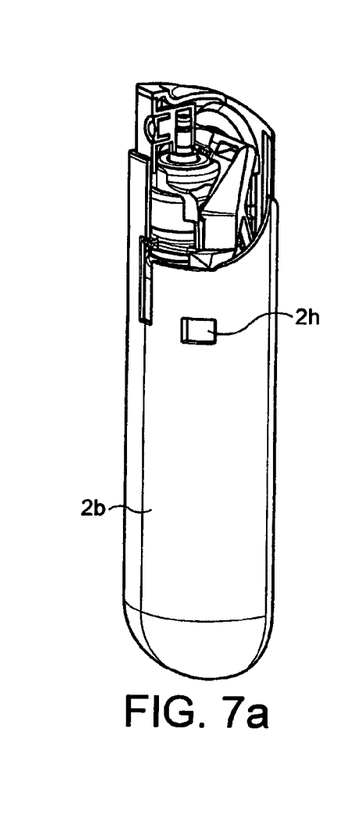
Figures 7B, 7C:
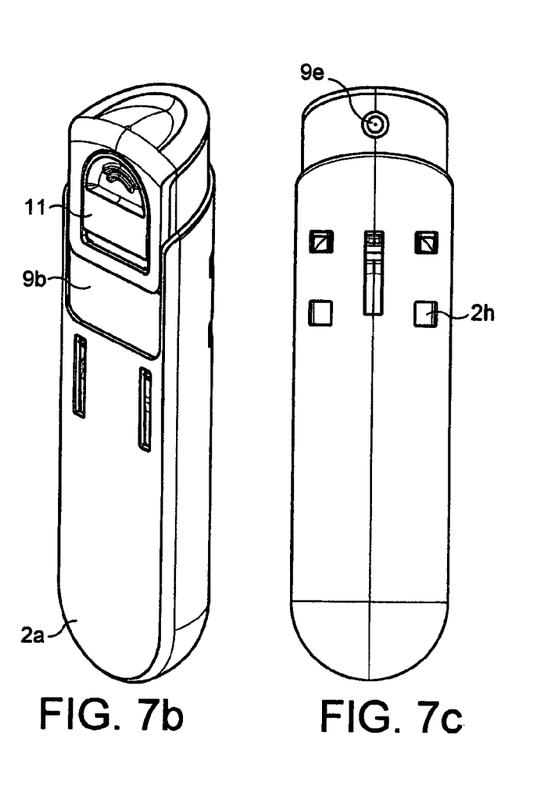
Figure 7D:
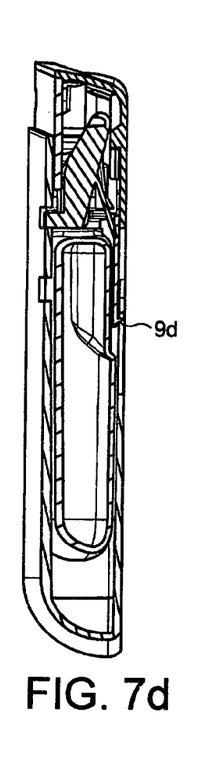
Figure 7E:
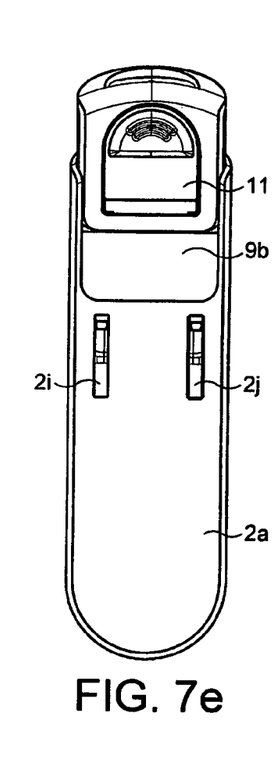

In this non-use position, the dispenser head 8, specifically the cap portion 10, blocks the opening 2c in the housing 2 and the curved front wall 2b of the housing 2 covers the outlet 9e in the front wall 9a of the face portion 9, shielding the outlet 9e and preventing access to the interior of the housing 2 (and hence to the phial 4, pump mechanism 5, collar 6 and locking lever 7). At the same time, the ridge 10c (see FIGS. 2b and 5b) and lower edge of the cut away section of the rear wall 2a of the housing 2 act respectively as a stop and abutment for preventing actuating movement of the dispenser head 8 towards the phial 4 along the axis A. Actuation of the pump mechanism 5 is thereby prevented in the non-use position.

Referring specifically to FIG. 2d, the locking lever 7 acts to lock the dispenser 3 in the non-use position. Thus, the elongate resilient elements 7h, 7i, reacting against the rear wall 9b, urge the locking lever 7 into a forward, locking position wherein the feet 7d, 7e engage the respective lower pair of apertures 2g, 2h to prevent relative sliding movement of the dispenser 3 and housing 2 along the axis A.

FIGS. 3 to 7 present a step-by-step illustration of the movement of the dispenser 3 from its non-use position shown in FIG. 2, to an operative position, shown in FIG. 7, in which the outlet 9e is uncovered.

Referring first of all to FIGS. 3 and 4, moving the locking lever 7 out of the locking position shown in FIG. 2 requires a two-step movement of the transmission plate 11.

Firstly, as shown in FIGS. 3a to 3e, the transmission plate 11 must be slid down a distance x (see also FIG. 1c), against the bias of the sprung metal member 12, to the position shown in FIG. 3, where the transmission plate 11 abuts against the steps 10j and the lower edge of the arched window 10c, and the curved upper edge of the transmission plate 11 "clears" the shoulder 10e (refer to FIG. 1c). From this position, the transmission plate 11 can then be tilted inwardly, on the hinged frame 10f, towards the locking lever 7, such that the upper region of the frame 10f and the transmission plate 11 engage the yoke portion 7c of the locking lever 7 and subsequently rotate the locking lever 7 out of the locking position, against the action of the resilient, elongate resilient elements 7h, 7i (see FIGS. 4a to 4e). In this manner, the feet 7d, 7e are moved out of latching engagement with the housing 2 (see FIG. 4d in particular).

It will be appreciated that a user may perform the above two movements manually using a single hand. Thus, a user may grasp the housing 2 (which acts as a handle) with one hand and then use his or her respective thumb to slide the transmission plate 11 down into the position shown in FIGS. 3a to 3e and subsequently press the transmission plate 11 (on the frame 10f) inwardly to move the feet 7d, 7e out of latching engagement with the housing 2 in the manner described and shown in FIG. 4.

With the transmission plate 11 in the position shown in FIGS. 4a to 4e, the dispenser 3 is no longer locked to the housing 2, and it is then a straightforward matter for the user to telescopically slide the dispenser 3 along the axis A, relative to the housing 2, using the same thumb to telescopically slide the dispenser 3 whilst continuing to press the transmission plate 11 inwardly. The dispenser 3 can thus be moved to the operational position shown in FIGS. 5a to 5e, wherein the guide projection 4e and slide projections 9d have reached the top of the central slot 2d and guide slots 2i. 2j respectively to limit further upward sliding movement of the dispenser 3 relative to the housing 2. During sliding movement of the dispenser 3 along the axis A, the spring 5d maintains the dispenser head 8 and phial 4 in fixed spatial relation to one another.

In the operational position shown in FIGS. 5a to 5e, the dispenser head 8 projects outwardly through the opening 2c in the housing 2 and the outlet 9e is no longer covered by the housing 2. Nevertheless, it should be noted that the dispenser head 8 still blocks the opening 2c, so that access to the interior of the housing 2 continues to be prevented, even in the operational position.

Once a user has moved the dispenser head 8 into the operational position shown in FIGS. 5a to 5e, the user can then lock the dispenser 3 to the housing 2 in the operational position by performing the same two-step movement of the transmission plate 11, but in reverse. Thus, referring to FIGS. 6 and 7, the user can release manual pressure on the transmission plate 11 to allow outward tilting movement of the transmission plate 11 back to the position shown in FIGS. 4a to 4e, whereby the transmission plate 11 and frame 10d become disengaged from the locking lever 7 and the resilient toe portions urge the feet into latching engagement with the upper pair of apertures 2e, 2f in the housing 2. From this position, the user can then manually slide the transmission plate 11 back into the misaligned position shown in FIG. 3, whereby inward tilting movement of the transmission plate 11 is prevented by the shoulder 10e.

With the dispenser 3 locked in the operative position, as shown in FIG. 7, the user can grasp the housing 2 and selectively depress the dispenser head 8 (and consequently the pump piston member 5c) relative to the housing 2 (and consequently the phial 4, which is locked relative to the housing 2), against the action of the spring 5d, to actuate the pump mechanism 5 and dispense a desired amount of substance through the outlet 9e. The user can carry out this dispensing operation without having to manually maintain the dispenser 3 in the operative position because the dispenser 3 is actually locked in the operative position. At the same time, the user can carry out the dispensing operation without having to touch the phial 4.

Once a user has finished dispensing the substance, the dispenser 3 can then be released from its locked operative position and returned to a locked non-use position simply by reversing the steps described above. Here, it should be noted that as the user slides the dispenser 3 back into the housing 2, the spring 5d again serves to maintain the phial 4 and the dispenser head 8 in substantially fixed spaced relation to prevent actuation of the pump mechanism 5.

It will be appreciated that the "two-step" movement of the transmission plate 11 which is required to move the feet of the locking lever 7 into and out of latching engagement with the housing 2 reduces the likelihood of accidental movement of the dispenser 3 from the non-use position to the operative position, for example when the dispenser is being carried in a pocket or handbag. Similarly, the "two-step" movement makes it more difficult for a child to "unlock" the dispensing device in the non-use position, either inadvertently or intentionally; the design thus provides a degree of "child resistance", which may be particularly advantageous where the substance is a medical substance such as, for example, a nicotine formulation.

In the embodiment shown in FIGS. 1 to 7, the movement of the dispenser 3 from the non-use position to a dispensing position requires an additional three "steps" even once the dispensing device has been "unlocked". Thus, even if the dispenser is "unlocked" in the non-use position, the housing 2 will continue to shield the outlet until such time as the dispenser 3 is manually moved to the operative position (which itself requires continued pressure applied to the transmission plate 11). In addition, because the sliding movement of the dispenser 3 is along the line of actuating movement of the dispenser head 8 relative to the dispenser body (and the spring 5d is configured for maintaining a fixed spatial relation between the dispenser head 8 and the phial 4 during such sliding movement of the dispenser 3) the pump mechanism 5 cannot effectively be actuated even with the dispenser 3 in the operative position, until such time as the dispenser 3 is locked in the operative position by a further "two-step" movement of the transmission plate 11. These additional steps further reduce the risk of unintentional or undesired actuation of the dispensing mechanism to dispense the substance out through the outlet 9e.

Although the housing may be any desired shape, it will be appreciated that the housing 2 preferably has a "slim-line" shape that is particularly ergonomic and space efficient. Indeed, it should be noted also that the dispensing device 1 has an "in-line" configuration, in that both sliding movement of the dispenser 3 relative to the housing 2 and actuating movement of the dispenser head 8 relative to the dispenser body are co-axial (each being directed along axis A). The "in-line" configuration of the dispensing device 1 is made possible by the feature that the dispenser 3 can be locked in the operative position, to prevent retraction of the dispenser 3 from the operative position when the dispenser head 8 is depressed, as well as the feature that the spring 5d has sufficient "stiffness" to maintain the dispenser head 8 and the phial 4 in fixed spatial relation during sliding movement of the dispenser 3 from the non-use position to the operative position.

It will be appreciated that, because the housing 2 is separate from the phial 4, the housing 2 is not restricted to being formed from materials that are specifically suitable for contact with the substance in the phial 4. This separation of the handle, being the part a user grasps to use the device, and the dispenser body, being the component defining the dispensing chamber, provides for greater flexibility in the use of materials. For example, the housing 2 may be formed from a material which lends itself to the formation of an ergonomic shape at relatively low cost, or a material which is highly shock resistant, without consideration of the material being "substance-inert".

In the case of the housing 2, the flat rear wall 2a allows the dispensing device to be safely laid flat on a surface, such as a table, without risk of the device 1 rolling off the surface.

In an alternative embodiment, the transmission plate may be omitted entirely, so that a user may directly engage the locking lever with his or her thumb, through the window in the peripheral skirt.

Although it is preferable that the actuating member be resiliently mounted to the dispenser body, for convenient actuation, it should be appreciated that this is not an essential feature of the invention, provided the actuating member is mounted for movement relative to the dispenser body to actuate the dispensing mechanism.

Whilst it is envisaged that the dispensing device will be assembled from "snap-fitting" together of components wherever possible, assembly of the dispensing device might also include other methods of attaching the various components, in particular gluing components together where appropriate.

The invention claimed is:

1. A hand-held dispensing device for dispensing a substance, said device comprising:
   a housing;
   a dispenser incorporating:
   i) a dispenser body defining a dispensing chamber for holding the substance;
   ii) an outlet in communication with said dispensing chamber;
   iii) a dispensing mechanism for dispensing the contents of said dispensing chamber through said outlet; and
   iv) an actuating member mounted for movement relative to said dispenser body to actuate said dispensing mechanism; and
   a locking assembly for releasably locking said dispenser body relative to said housing to prevent manual sliding movement of said dispenser body relative to said housing in at least a first, operative position of said dispenser in which said actuating member is movable relative to said dispenser body to actuate said dispensing mechanism to dispense the substance through said outlet to a user, whereby a user may grasp said housing and effect manual movement of said actuating member relative to said housing and said dispenser body to actuate said dispensing mechanism to dispense the contents of said dispensing chamber through said outlet;
   wherein:
   said dispenser, as a unit, is movable between said first, operative position and a second, non-use position in which the substance cannot be dispensed through said outlet to a user; and
   said actuating member is in the form of a dispenser head incorporating said outlet, said dispenser head being mounted at one end of said dispenser body for manual depression relative to said dispenser body to actuate said dispensing mechanism.

2. A device according to claim 1, wherein said locking assembly is further configured for releasably locking said dispenser body relative to said housing in said non-use position to prevent manual sliding movement of said dispenser relative to said housing and into said operative position.

3. A device according to claim 2, wherein said actuating member is provided with a stop that engages an abutment on said housing when said dispenser is in said non-use position for preventing actuating movement of said actuating member relative to said dispenser body.

4. A hand-held dispensing device according to any one of claims 1-3, wherein:
   said actuating member is resiliently mounted for movement relative to said dispenser body against the action of a biasing member; and
   with said dispenser in said operative position, a user may effect said manual movement of said actuating member relative to said housing and said dispenser body, against the action of said biasing member.

5. A device according to claim 4, wherein said dispenser is operably connected to said housing for relative, manual, sliding movement along a line of action of said biasing member, said biasing member being configured for maintaining said dispenser body and actuating member in substantially fixed, spatial relation to one another during said sliding movement from said non-use position to said operative position.

6. A device according to claim 1, wherein:
   said housing is hollow and slidably receives said dispenser; and
   said dispenser is manually slidable between said operative position, in which said dispenser head projects outwardly through an opening in said housing, and said non-use position, in which said dispenser is retracted within said housing.

7. A device according to claim 6, wherein said dispenser head is resiliently mounted at one end of said dispenser body for manual depression relative to said dispenser body, against the action of a biasing member, to actuate said dispensing mechanism, and wherein said manual sliding movement of said dispenser between said operative position and said non-use position is along the axis of depression of said dispenser head, said biasing member being configured for maintaining said dispenser head and dispenser body in substantially fixed, spatial relation to one another during said manual sliding movement.

8. A device according to claim 6, wherein:
   said dispenser head extends through an opening in the top of said housing; and
   said dispenser head is configured to block said opening in said housing when said dispenser is retracted to said non-use position.

9. A device according to claim 8, wherein said dispenser head is dimensioned to engage said housing in a telescopic fit, the length of said dispenser head being such that said dispenser head blocks said opening in said housing over the full range of manual sliding movement of said dispenser between said non-use position and said operative position.

10. A device according to claim 9, wherein said housing has a wall with a section with a cut-away adjacent said opening such that a user may manually engage said dispenser head directly in said retracted, non-use position and effect manual sliding movement of said dispenser head, relative to said housing, to move said dispenser from said non-use position to said operative position.

11. A device according to claim 9, wherein:
    said dispenser head comprises a peripheral skirt defining a hollow interior head region communicating with the interior of said housing; and
    said locking assembly comprises a locking lever mounted to said dispenser body at a fulcrum located inside said hollow interior head region, said locking lever having a latching element which is displaceable, by pivotal movement of said locking lever, into and out of latching engagement with said housing.

12. A device according to claim 11, wherein said locking lever is urged by a resilient element in a direction to displace said latching element into latching engagement with said housing.

13. A device according to claim 12, wherein:
said housing has a wall with a section with a cut-away adjacent said opening such that a user may manually engage said dispenser head directly in said retracted, non-use position and effect manual sliding movement of said dispenser head, relative to said housing, to move said dispenser from said non-use position to said operative position;
said peripheral skirt is provided with a window which is aligned with said cut-away section of said housing; and
a user may apply manual pressure to said locking lever, through said cut-away section and said window in said peripheral skirt, to effect said pivotal movement of said locking lever against the action of said resilient element in the direction to displace said latching element away from latching engagement with said housing.

14. A device according to claim 13, wherein a transmission plate is displaceably mounted on said peripheral skirt at said window, for transmitting to said locking lever said manual pressure applied to said transmission plate.

15. A device according to claim 14, wherein said transmission plate is hingedly mounted on the exterior of said peripheral skirt and dimensioned for inward tilting movement through said window to engage said locking lever.

16. A device according to claim 15, wherein said transmission plate is slidably mounted on said peripheral skirt for sliding movement relative to said window between an aligned position, allowing said inward tilting movement of said transmission plate through said window, and a mis-aligned position, in which the edge of said window prevents inward tilting movement of said transmission plate through said window.

17. A device according to claim 16, wherein said transmission plate is resiliently biased towards said mis-aligned position and is slidable against the action of said bias into said aligned position.

18. A device according to any one of claims 1-3, wherein the exterior of said housing incorporates a flat face-section.

19. A device according to any one of claims 1-3, wherein said dispensing mechanism is a pump mechanism and said outlet is a spray nozzle.

20. A device according to any one of claims 1-3, wherein said dispensing chamber contains a substance in liquid form.

21. A device according to claim 20, wherein the substance comprises a nicotine formulation or other formulation.

22. A device according to claim 21, wherein the substance comprises a nicotine formulation, and wherein the dispenser body is made from a material selected from one or more of or a mixture of glass, a copolymer of acrylonitrile and methyl acrylate (Barex®), a cyclic olefin copolymer (COC), polymers based on dimethyl-2,6 naphthalene dicarboxylate or 2,6-naphthalene dicarboxylic acid monomers, such as polyethylene naphthalate (PEN) and polytrimethylene naphthalate (PTN), liquid crystal polymers (LCP), preferably LCPs comprising hydroxy benzoic acid and hydroxy naphthalenic acid, said materials being optionally mixed with one or more of polymers, selected from polyacrylonitrile (PAN), polyamide (PA), polyvinylidene chloride (PVDC), fluoropolymers, ethylene vinyl alcohol copolymer (EVOH), polyvinyl alcohol (PVA), ionomers, polyethylene (PE), polypropylene (PP) and polyethylene terephtalate (PET).

23. A device according to any one of claims 1-3, wherein said dispenser is operably connected to said housing for manual sliding movement relative to said housing from a non-use position, in which said housing covers said outlet, to an operative position, in which said outlet is uncovered.

24. A device according to claim 10, wherein:
said dispenser head is resiliently mounted at one end of said dispenser body for manual depression relative to said dispenser body against the action of a biasing member; and
said biasing member maintains said dispenser body and dispenser head in substantially fixed relation during said sliding movement of said dispenser relative to said housing.

25. A hand-held dispensing device for dispensing a substance, said device comprising:
a handle; and
a dispenser incorporating:
i) a dispenser body defining a dispensing chamber for holding the substance;
ii) an outlet in communication with said dispensing chamber;
iii) a dispensing mechanism for dispensing the contents of said dispensing chamber through said outlet; and
iv) an actuating member mounted for movement relative to said dispenser body to actuate said dispensing mechanism; and
wherein:
said actuating member is mounted at one end of said dispenser body for manual depression relative to said dispenser body along an actuation axis to actuate said dispensing mechanism;
said dispenser, as a unit, is movable relative to said handle, in a direction at least parallel to said actuation axis, between (i) a first, operative position in which said actuating member is movable relative to said dispenser body to actuate said dispensing mechanism to dispense the substance through said outlet to a user, and (ii) a second, non-use position in which the substance cannot be dispensed through said outlet to a user;
in said second, non-use position said handle covers said outlet; and
in said first, operative position said dispenser is moved into a position in which said outlet is no longer covered by said handle.

26. A device according to claim 10, further comprising a locking assembly for releasably locking said dispenser body relative to said handle to prevent manual sliding movement of said dispenser body relative to said handle when said dispenser is in at least said first, operative position, whereby a user may grasp said handle and effect manual movement of said actuating member relative to said handle and said dispenser body to actuate said dispensing mechanism and dispense the contents of said dispensing chamber through said outlet without causing said dispenser body to move relative to said handle.

27. A device according to claim 26, wherein said locking assembly releasably locks said dispenser body relative to said handle to prevent manual sliding movement of said dispenser body relative to said handle when said dispenser is in said second, operative position.

28. A device according to any one of claims 25-27, wherein said handle is a hollow housing and said dispenser fits telescopingly therein to slide between said first, operative position and said second, non-use position.

29. A device according to claim 25, further comprising a biasing member positioned between said actuating mechanism and said dispenser body, said actuating member being movable against the action of said biasing member when said dispenser is in said first, operative position to actuate said dispensing mechanism.

30. A device according to claim 25, wherein said actuating member is prevented from moving relative to said dispenser body when said dispenser is in said second, non-use position.

31. A device according to claim 30, wherein a portion of said handle prevents movement of said actuating member relative to said dispenser body when said dispenser is in said second, non-use position.

32. A device according to claim 31, wherein in said first, operative position said actuating member is spaced away from said portion of said handle and thereby is movable relative to said dispenser body.

33. A hand-held dispensing device for dispensing a substance, said device comprising:
   a housing;
   a dispenser incorporating:
      i) a dispenser body defining a dispensing chamber for holding the substance;
      ii) an outlet in communication with said dispensing chamber;
      iii) a dispensing mechanism for dispensing the contents of said dispensing chamber through said outlet; and
      iv) an actuating member mounted for movement relative to said dispenser body to actuate said dispensing mechanism; and
   a locking assembly for releasably engaging said dispenser and said housing together, to prevent relative movement therebetween, alternately in (i) a non-use position of said dispenser in which the substance cannot be dispensed through said outlet to a user; and (ii) an operative position of said dispenser in which said actuating member is movable relative to said dispenser body to actuate said dispensing mechanism to dispense the substance through said outlet to a user, whereby a user may grasp said housing and effect manual movement of said actuating member relative to said housing and said dispenser body to actuate said dispensing mechanism and dispense the contents of said dispensing chamber through said outlet;
   wherein:
   said dispenser, as a unit, is movable between said operative position and said non-use position;
   said dispenser is locked against movement relative to said housing in said operative position and in said non-use position;
   said locking assembly comprises a locking lever mounted to said dispenser body and having a latching element displaceable into and out of latching engagement with said housing.

34. A device according to claim 33, further comprising a transmission plate mounted for pivoting and sliding movement with respect to said dispenser, wherein:
   said locking lever is pivotably mounted to said dispenser body;
   pivoting of said transmission plate causes pivoting of said locking lever to engage or to disengage said latching element into and out of latching engagement with said housing; and
   said transmission plate is mounted for sliding between a blocked position in which said transmission plate is prevented from pivoting said locking lever, and an unblocked position in which said transmission plate is free to pivot said locking lever.

* * * * *